United States Patent
Voellmicke et al.

(10) Patent No.: US 8,133,280 B2
(45) Date of Patent: Mar. 13, 2012

(54) METHODS AND DEVICES FOR EXPANDING A SPINAL CANAL

(75) Inventors: John C. Voellmicke, Cumberland, RI (US); Michael A. Slivka, Taunton, MA (US); Michael A. Fisher, Middleborough, MA (US)

(73) Assignee: DePuy Spine, Inc., Raynham, MA (US)

( * ) Notice: Subject to any disclaimer, the term of this patent is extended or adjusted under 35 U.S.C. 154(b) by 571 days.

(21) Appl. No.: 12/339,503

(22) Filed: Dec. 19, 2008

(65) Prior Publication Data
US 2010/0161056 A1   Jun. 24, 2010

(51) Int. Cl.
*A61F 2/44* (2006.01)

(52) U.S. Cl. ...................... 623/17.11; 606/246

(58) Field of Classification Search .... 623/17.11–17.16; 606/60, 246–249
See application file for complete search history.

(56) References Cited

U.S. PATENT DOCUMENTS

| | | | |
|---|---|---|---|
| 4,349,921 A * | 9/1982 | Kuntz | 623/17.16 |
| 5,085,660 A | 2/1992 | Lin | |
| 5,366,455 A | 11/1994 | Dove et al. | |
| 5,470,333 A | 11/1995 | Ray | |
| 5,507,747 A | 4/1996 | Yuan et al. | |
| 5,527,312 A | 6/1996 | Ray | |
| 5,531,745 A | 7/1996 | Ray | |
| 5,531,747 A | 7/1996 | Ray | |
| 5,558,674 A | 9/1996 | Heggeness et al. | |
| 5,609,636 A * | 3/1997 | Kohrs et al. | 623/17.16 |
| 5,704,936 A | 1/1998 | Mazel | |
| 6,080,157 A * | 6/2000 | Cathro et al. | 606/279 |
| 6,306,170 B2 * | 10/2001 | Ray | 623/17.11 |
| 6,355,038 B1 | 3/2002 | Pisharodi | |
| 6,375,655 B1 * | 4/2002 | Zdeblick et al. | 623/17.16 |
| 6,440,135 B2 | 8/2002 | Orbay et al. | |
| 6,458,131 B1 | 10/2002 | Ray | |
| 6,572,617 B1 | 6/2003 | Senegas | |

(Continued)

FOREIGN PATENT DOCUMENTS

EP      599640      6/1994

(Continued)

OTHER PUBLICATIONS

Frank et al., "A technique for cervical laminoplasty using mini plates," British Journal of Neurosurgery 8:197-199 (1994).

(Continued)

*Primary Examiner* — Eduardo C Robert
*Assistant Examiner* — Ellen C Hammond
(74) *Attorney, Agent, or Firm* — Nutter McClennen & Fish LLP

(57) ABSTRACT

Devices and methods are disclosed for expanding a spinal canal. An implantable device having a shaft with a first cross-sectional dimension distinct from a second cross-sectional dimension can be inserted into an opening in a lamina and rotated 90 degrees to hinge the lamina away from the spinal canal. The implant can have one or more radiused edges, a bulleted tip, one or more lateral extensions for fastening the implantable device to bone, one or more hinged lateral extensions, one or more arcuate protrusions for biting into adjacent bone, an enlarged proximal head to prevent over-insertion, and/or a sleeve disposed therearound to reduce friction. Various embodiments of an insertion apparatus that can be selectively coupled to the implantable device are also disclosed, along with methods of expanding a spinal canal in minimally-invasive procedures using an implantable device and/or an insertion apparatus.

11 Claims, 14 Drawing Sheets

U.S. PATENT DOCUMENTS

| | | |
|---|---|---|
| 6,610,091 B1 | 8/2003 | Reiley |
| 6,626,909 B2 | 9/2003 | Chin |
| 6,635,087 B2 * | 10/2003 | Angelucci et al. ......... 623/17.11 |
| 6,660,007 B2 * | 12/2003 | Khanna ......................... 606/284 |
| 6,669,697 B1 | 12/2003 | Pisharodi |
| 6,712,820 B2 | 3/2004 | Orbay |
| 6,712,852 B1 * | 3/2004 | Chung et al. ............... 623/17.11 |
| 6,719,795 B1 | 4/2004 | Cornwall et al. |
| 6,767,351 B2 | 7/2004 | Orbay et al. |
| 6,811,567 B2 | 11/2004 | Reiley |
| 6,923,810 B1 * | 8/2005 | Michelson ................... 606/247 |
| 6,955,691 B2 * | 10/2005 | Chae et al. ................. 623/17.16 |
| 6,974,478 B2 | 12/2005 | Reiley et al. |
| 7,063,725 B2 * | 6/2006 | Foley ......................... 623/17.16 |
| 7,074,239 B1 | 7/2006 | Cornwall et al. |
| 7,087,084 B2 | 8/2006 | Reiley |
| 7,090,676 B2 | 8/2006 | Huebner et al. |
| 7,264,620 B2 * | 9/2007 | Taylor ......................... 606/86 A |
| 7,331,996 B2 * | 2/2008 | Sato et al. .................. 623/17.16 |
| 7,674,295 B2 * | 3/2010 | Eckman ...................... 623/17.11 |
| 8,007,537 B2 * | 8/2011 | Zucherman et al. ....... 623/17.16 |
| 2002/0120335 A1 * | 8/2002 | Angelucci et al. ......... 623/17.16 |
| 2003/0045935 A1 | 3/2003 | Angelucci et al. |
| 2003/0125738 A1 | 7/2003 | Khanna |
| 2004/0030388 A1 * | 2/2004 | Null et al. ................... 623/17.11 |
| 2004/0102775 A1 | 5/2004 | Huebner |
| 2004/0210222 A1 * | 10/2004 | Angelucci et al. .............. 606/69 |
| 2005/0085818 A1 | 4/2005 | Huebner |
| 2005/0107877 A1 | 5/2005 | Blain |
| 2005/0119657 A1 | 6/2005 | Goldsmith |
| 2005/0131412 A1 | 6/2005 | Olevsky et al. |
| 2005/0149021 A1 | 7/2005 | Tozzi |
| 2005/0182407 A1 | 8/2005 | Dalton |
| 2005/0251138 A1 | 11/2005 | Boris et al. |
| 2005/0273100 A1 | 12/2005 | Taylor |
| 2007/0123869 A1 | 5/2007 | Chin et al. |
| 2008/0009865 A1 | 1/2008 | Taylor |
| 2008/0215096 A1 * | 9/2008 | Nash et al. .................... 606/249 |
| 2009/0210012 A1 * | 8/2009 | Null et al. ...................... 606/280 |
| 2011/0046680 A1 * | 2/2011 | Khanna ......................... 606/279 |

FOREIGN PATENT DOCUMENTS

| | | |
|---|---|---|
| WO | 9709940 | 3/1997 |
| WO | 03020142 | 3/2003 |
| WO | 03101319 | 12/2003 |
| WO | 2005041752 | 5/2005 |
| WO | 2005096969 | 10/2005 |
| WO | 2006104487 | 10/2006 |

OTHER PUBLICATIONS

Shaffrey, M.D. et al., "Modified open-door laminoplasty for treatment of neurological deficits in younger patients with congenital sinpal stenosis: analysis of clinical and radiographic data," J. Neurosurg. (Spine 2) 90:170-177 (1999).

* cited by examiner

METHODS AND DEVICES FOR EXPANDING A SPINAL CANAL

FIELD OF THE INVENTION

The present invention relates to methods and devices for use in surgery, and more specifically to methods and devices for expanding a spinal canal.

BACKGROUND OF THE INVENTION

In certain pathologies, the spinal canal extending through a patient's vertebrae is or becomes too narrow and constricts the spinal cord extending therethrough. The narrowing may be congenital, potentially affecting patients at any age. Narrowing can also be attributable to other causes, such as age, injury or removal of a spinal disc.

A condition associated with aging, for instance, is spondylolsis, in which intervertebral discs lose water and become less dense. These degenerative changes near the disc can cause an overgrowth of the bone, producing bony spurs called, "osteophytes" that can compress the spinal cord. The constriction of the spinal cord in the cervical spine, for example, often produces pain, weakness, or loss of feeling in extremities. Other causes for narrowing of the spinal canal include disc shrinkage, which causes the disc space to narrow and the annulus to bulge and mushroom out, resulting in pressure on the spinal cord. Degenerative arthritis of facet joints can cause joints to enlarge, or the vertebrae to slip with respect to each other, also compressing the spinal cord. Instability between vertebrae, such as caused by stretched and thickened ligaments can also produce pressure on the spinal cord and nerve roots.

Myelopathy, or malfunction of the spinal cord, occurs due to its compression. The rubbing of the spine against the cord can also contribute to this condition, and the spinal cord compression can ultimately compromise the blood vessels feeding the spinal core, further aggravating the myelopathy.

Traditional procedures for decompressing the spinal cord include a laminectomy, in which the lamina and spinal processes are removed to expose the dura covering the spinal cord. Laminectomies, however, can lead to instability and subsequent spinal deformity. Another known procedure is a laminoplasty, in which the lamina is lifted off the dura, but not completely removed. Typically, one side of the lamina is cut, while a partial cut is made on the other side to hinge the lamina away from the spinal cord to increase the size of the spinal canal. A strut of bone can be placed in the open portion within the lamina and the facet to help hold the open position of the lamina. Laminoplasties preserve more of the bone, muscle, and ligaments, but current techniques and devices are cumbersome and require exceptional technical skills, particularly for performing minimally invasive techniques.

Accordingly, improved methods and devices for expanding the spinal canal are needed, and in particular, methods and devices that can be used in minimally-invasive surgery.

SUMMARY OF THE INVENTION

The systems and methods disclosed herein can be useful for expanding a spinal canal. In one embodiment an implantable device is provided for expanding a spinal canal. The implantable device includes an elongate body having a head and a shaft. The shaft can have a cross-section taken perpendicular to the longitudinal axis of the body such that the cross-section has a first dimension distinct from a second dimension and has at least two diagonally-opposite radiused corners. The head can have a driver interface at a proximal end thereof with a torque receiving surface. In an exemplary embodiment, the cross-section of the shaft can be substantially rectangular and the head can have a dimension larger than the shaft to prevent over-insertion of the body into an opening. Additionally, the body can include an osteointegration-promoting coating and/or can be formed of a resorbable material.

In another exemplary embodiment, the elongate body can have at least one arcuate protrusion formed thereon that is configured to engage bone as the body is rotated within an opening. The body can also include at least one lateral extension at its proximal end, the lateral extension having at least one opening formed therein for receiving at least one fastening element. The at least one opening can have a variety of characteristics. For example, it can be in the form of an elongate slot or a polyaxial seat. In one embodiment, the at least one lateral extension can be attached to the proximal end of the body with a hinge such that the extension is rotatable about the hinge.

In another exemplary embodiment, the implantable device can include a sleeve disposed around the body such that the body is rotatable within the sleeve.

In yet another embodiment, a method is provided for expanding a spinal canal. The method can include forming an opening in a first side of a lamina of a spine, inserting an implant into the opening in a first orientation in which the implant fits within the opening in a clearance fit, and rotating the implant to a second orientation in which the implant expands the size of the opening, thereby expanding the spinal canal. The implant can be rotated in a variety of ways, and in one embodiment it can be rotated 90 degrees. In an exemplary embodiment, rotating the implant can cause at least one arcuate protrusion formed thereon to engage a wall of the opening. Alternatively or in addition, rotating the implant can cause the lamina to cam over at least one radiused corner of the implant.

In one embodiment, the implant can be inserted distally into the opening until a lip at the proximal end of the implant prevents further insertion. The implant can be inserted into the opening using an insertion apparatus selectively attached to the implant.

In another embodiment, the method can further include forming a relief in a second side of the lamina opposite the first side before inserting the implant to permit the lamina to hinge posteriorly away from the spinal canal. The method can also include accessing the vertebral body using at least one minimally invasive portal and/or securing the implant to the vertebral body to prevent post-operative movement of the implant. Securing the implant can include unfolding at least one hinged lateral extension of the implant after inserting the implant into the opening and attaching the at least one hinged lateral extension to the vertebral body with at least one bone screw.

In certain embodiments, inserting the implant can include first inserting a sleeve into the opening and then inserting the implant into the sleeve. Alternatively, inserting the implant can include inserting the implant and a sleeve disposed therearound simultaneously.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In general, various devices and methods are provided for expanding a spinal canal by inserting an implantable device into an opening in a lamina and rotating the implantable device to expand the opening. In one exemplary embodiment, an implantable device for expanding a spinal canal is provided that includes an elongate body having a head and a shaft. The shaft of the elongate body can have a cross-section taken perpendicular to its longitudinal axis that has a first dimension to allow insertion between cut ends of a lamina that is distinct from a second dimension sufficient to open and hold open a spinal canal. For example, the shaft can have a generally rectangular cross-section, can be oval in cross-section, or can have virtually any other cross-sectional shape in which one dimension is greater than another. When a shaft having such a cross-section is inserted into an opening in a first orientation and then rotated 90 degrees about the axis of insertion to a second orientation, the opening can be spread apart or expanded accordingly.

Figure 1A:
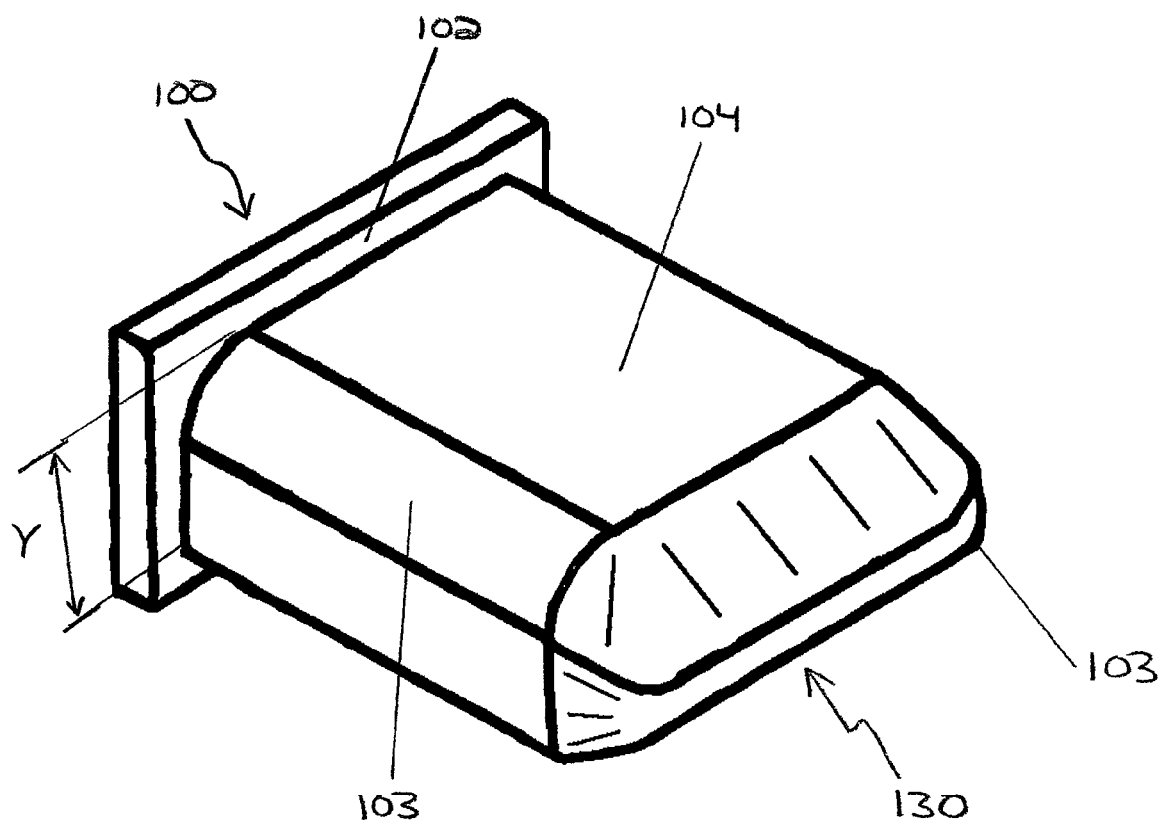
FIG. 1A is a perspective view of one embodiment of an implantable device for expanding a spinal canal.
Figure 1B:
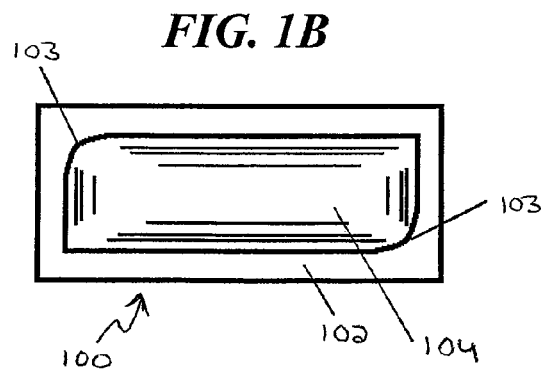
FIG. 1B is an elevation view of the distal end of the implantable device of FIG. 1A.
Figure 1C:
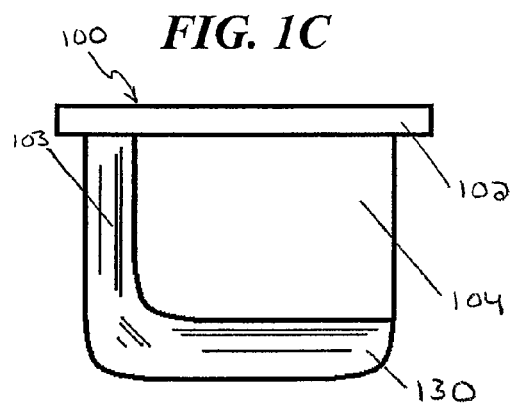
FIG. 1C is a plan view of the implantable device of FIG. 1A.

FIG. 1A illustrates one exemplary embodiment of an implantable device 100 in accordance with the present invention. As shown, the implantable device 100 includes a head 102 and a shaft 104. The distal tip 130 of the shaft 104 can be bulleted or rounded to act as a wedge, thereby facilitating insertion into a space having an initial dimension smaller than the height Y of the shaft 104. The shaft 104 can also have one or more radiused edges 103 to facilitate rotation within a bone opening, as will be discussed in further detail below. In the illustrated embodiment, as shown in FIG. 1B, two diagonally opposed corners 103 of the otherwise rectangular shaft 104 are rounded or radiused. As shown in FIG. 1C, the head 102 of the device 100 can have a dimension larger than the shaft 104 such that it is configured to prevent over-insertion into an opening. FIG. 1E illustrates a cross-section of the shaft 104 of the implantable device 100. As shown, the shaft 104 has a cross section having a first dimension (i.e., width) X that is distinct from a second dimension (i.e., height) Y.

Figure 1D:
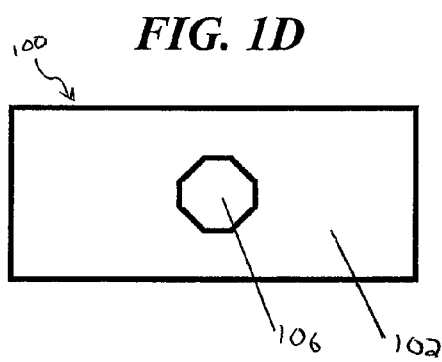
FIG. 1D is an elevation view of the proximal end of the implantable device of FIG. 1A.
Figure 1E:
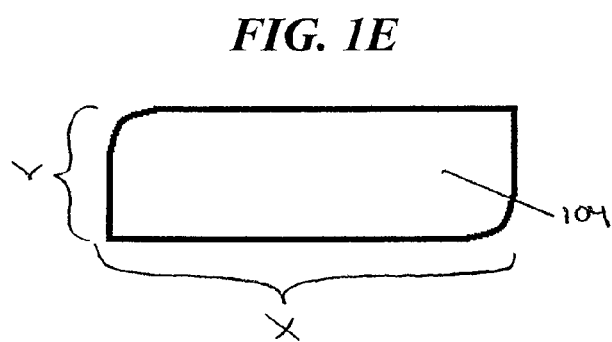
FIG. 1E is a cross-sectional view of the shaft of the implantable device of FIG. 1A.
Figure 1F:
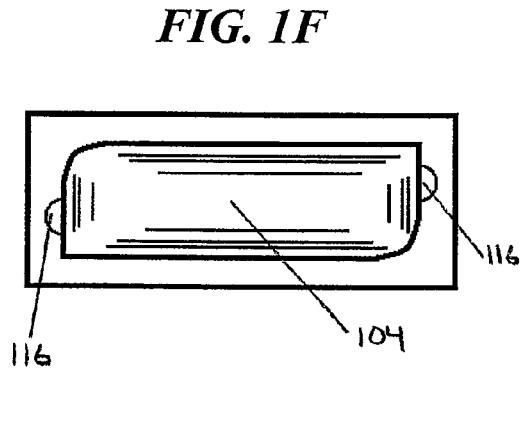
FIG. 1F is an elevation view of the distal end of one embodiment of an implantable device having arcuate protrusions formed thereon.
Figure 1G:
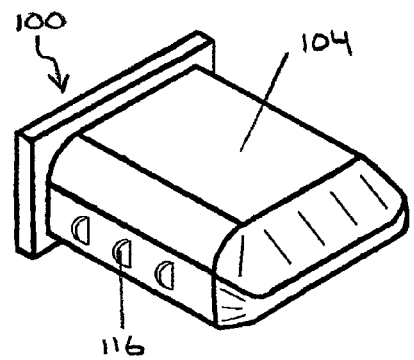
FIG. 1G is a perspective view of the implantable device of FIG. 1F.

As shown in FIGS. 1F-1G, the shaft 104 can optionally include one or more protrusions 116 formed thereon configured to engage surrounding bone as the shaft is rotated within a bone opening. In the illustrated embodiment, the protrusions 116 are in the form of shallow arcuate fins angled in the direction of rotation and configured to superficially bite into the interior walls of the bone opening as the shaft is rotated therein. The protrusions 116 can also be angled opposite to the direction of rotation or there can be some protrusions angled in one direction while others are angled in the opposite direction.

As shown in FIG. 1D, the head 102 of the implantable device 100 can include a driver interface 106 at a proximal end thereof with a torque receiving surface that is configured to permit selective coupling of the implantable device 100 to an insertion apparatus. The driver interface 106 can be either male or female. For purposes of illustration, FIG. D shows a female driver interface 106.

Figure 2A:
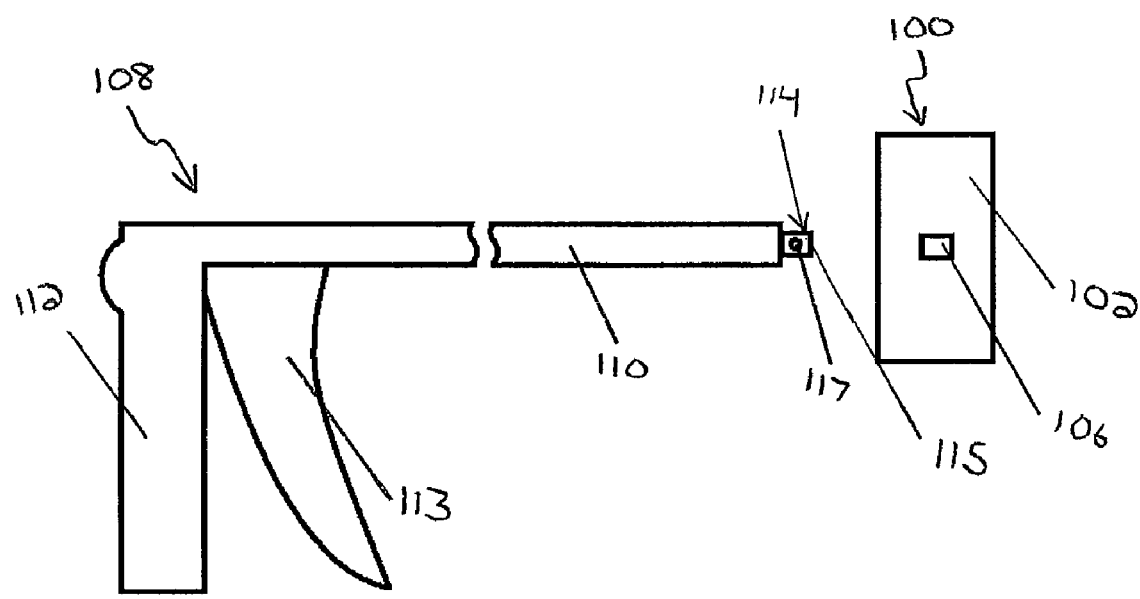
FIG. 2A is an elevation view of an implantable device and one embodiment of an insertion apparatus.

FIG. 2A illustrates one embodiment of an insertion apparatus 108 for inserting the implantable device 100 into a patient using a minimally invasive procedure. As shown, the insertion apparatus 108 can be in the form of an elongate body 110 having a handle portion 112 and a trigger 113 at its proximal end and an engagement member 114 at its distal end. The handle 112 and/or the elongate body 110 can be bayoneted or angled to improve visualization and/or ergonomics during a surgical procedure and can be sized to permit delivery of the implantable device through an access port in a minimally invasive procedure. In the illustrated embodiment, the engagement member 114 is in the form of a male protrusion 115 configured to selectively engage a female socket 106 formed in the head 102 of the implantable device 100. The protrusion 115 can selectively engage the socket 106 using any of a variety of techniques known in the art, including for example a friction fit, an interference fit, a threaded engagement, etc. In the illustrated embodiment, a small piston 117 is positioned in one side of the protrusion 115. The piston 117 can be actuated by the trigger 113 such that squeezing the trigger 113 can retract the piston 117 into the protrusion 115, thereby removing a friction or interference engagement of the piston 117 with a sidewall of the socket 106. Releasing the trigger 113 can be effective to force the piston 117 back out of the protrusion 115 and into a friction or interference engagement with the socket 106. The protrusion 115 can have a non-circular cross-section such that rotation of the insertion apparatus 108 causes a commensurate rotation of the implantable device 100 when the two are coupled together.

Figure 2B:
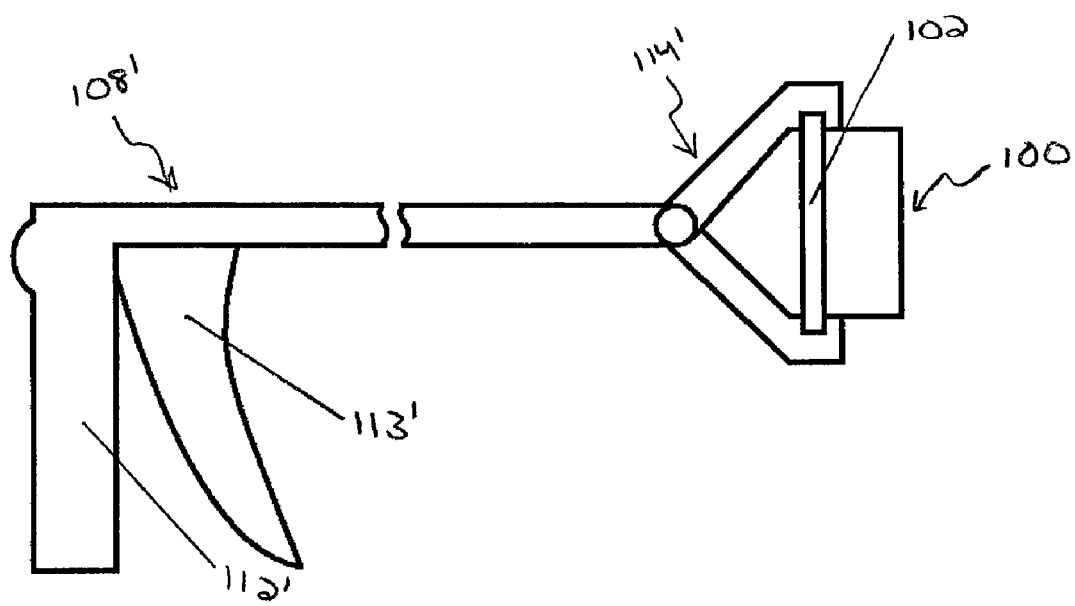
FIG. 2B is an elevation view of an implantable device and another embodiment of an insertion apparatus.

FIG. 2B illustrates another embodiment of an insertion apparatus 108'. As shown, the engagement member 114' of this embodiment includes opposed claws configured to grasp the edges of the head 102 of the implantable device 100. Squeezing the trigger 113' proximally towards the handle 112' can be effective to draw the claws together. Releasing the trigger 113' can be effective to spread the claws apart. One skilled in the art will appreciate that various other methods of selectively engaging the implantable device with an insertion apparatus can be used.

The implantable device can be formed of a variety of implantable materials, including resorbable materials, non-resorbable materials, and/or a combination thereof. The implantable device can be radiopaque to facilitate accurate insertion of the device in a minimally invasive surgery using fluoroscopy, can be radiolucent so as not to interfere with post-operative imaging procedures, or can be partially radiopaque and partially radiolucent. Exemplary materials that can be used in constructing the implantable device include metals such as titanium or stainless steel, non-resorbable polymers and composites such as polyetheretherketone (PEEK) and carbon-fiber reinforced PEEK, resorbable polymers such as polylactic acid and polyglycolic acid, ceramic materials such as aluminum oxide and hydroxyapatite, allograft materials derived from animal or human cortical or cancellous bone, and/or any combination thereof.

In one embodiment, the shaft of the implantable device can be 2-4 mm in height (i.e., Y dimension), 4-12 mm in width (i.e., X dimension), and 2-8 mm long. The implantable device can be sized so as to be insertable through an access port as part of a minimally invasive procedure.

In certain embodiments, the edges of the shaft that will contact the interior walls of a bone opening can be shaped to mate or otherwise substantially conform to the dimensions of the bone wall surface to help the device maintain a desired position both during the procedure and post-operatively. In one embodiment, these edges can be conformable to the interior walls of a bone opening by pre-attaching HEALOS (HA/collagen sponge) pieces thereto. HEALOS is an osteoconductive matrix constructed of cross-linked collagen fibers that are fully coated with hydroxyapatite and is available from DePuy Spine, Inc. of Raynham, Mass. Such pre-attached pieces can have the effect of promoting osteointegration between the implantable device and the surrounding bone. Alternatively, the edges can be coated with hydroxyapatite and/or a porous metal or polymer coating to elicit the same effect.

Figure 3A:
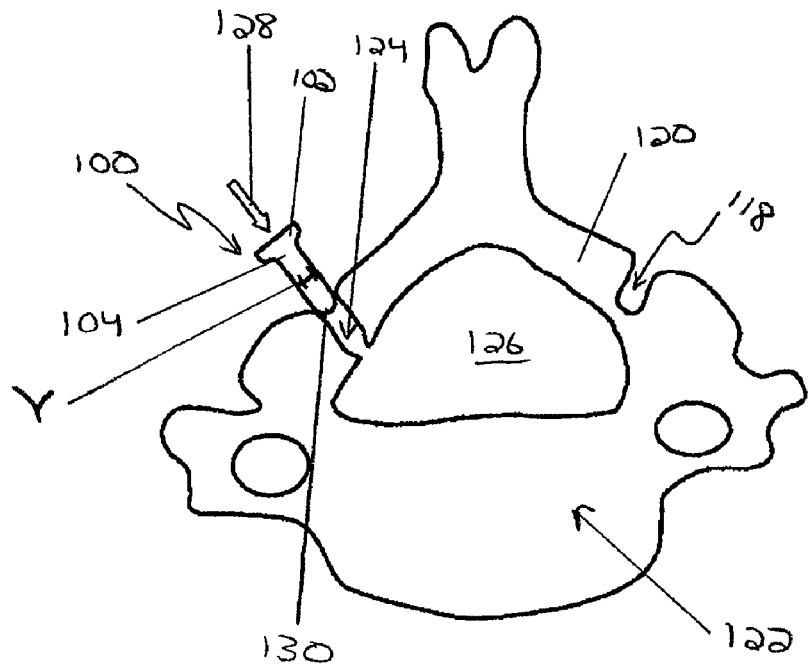
FIG. 3A is a plan view of a vertebral body and one embodiment of an implantable device partially inserted into an opening in a lamina.
Figure 3B:
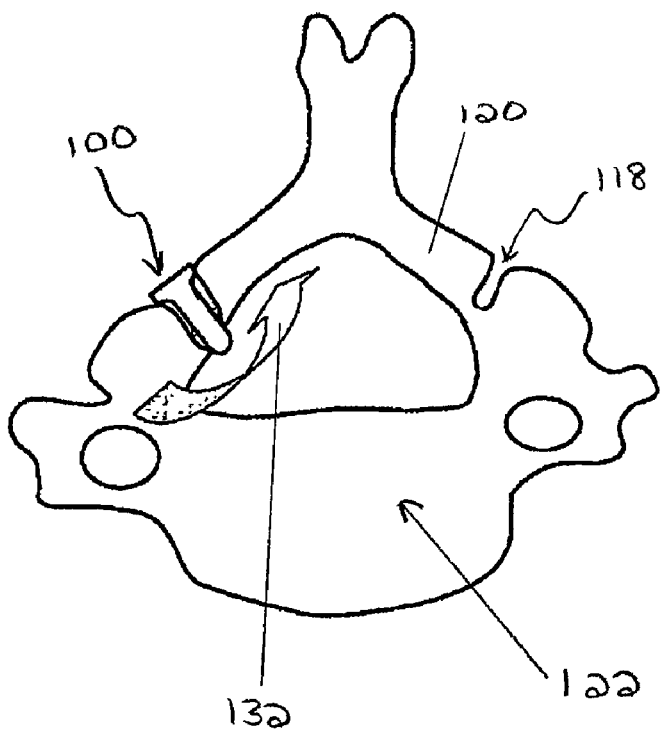
FIG. 3B is a plan view of the vertebral body of FIG. 3A with the implantable device fully inserted into the opening in the lamina.

In use, the implantable device 100 can be inserted into a relatively small opening formed in a lamina to force a portion of the lamina away from the spinal canal, thereby increasing the cross-sectional size of the spinal canal. In a typical laminoplasty procedure, as shown in FIG. 3A, a blind recess or "green stick" 118 is formed on a first side of a lamina 120 of a vertebral body 122 to act as a hinge. On a second side of the lamina 120, opposite the side containing the blind recess 118, an opening or osteotomy 124 is formed all the way through the lamina 120 to the dura of the spinal canal 126. With the vertebral body 122 prepared as described, the implantable device 100 can be advanced into the opening 124 towards the spinal canal 126 in the direction of arrow 128. The head 102 of the implantable device 100 can be made wider than the shaft 104 to prevent over-insertion. As shown, the leading edge of the head 102 will contact the mouth of the opening 124 before the distal bulleted tip 130 of the shaft 104 advances too far into the spinal canal 126, precluding further distal movement and providing the surgeon with mechanical feedback as to the position of the implantable device 100 within the opening 124. In the illustrated embodiment, the implantable device 100 has a first dimension Y that is slightly larger than the width of the opening 124. As the implantable device 100 is advanced into the opening 124, its bulleted tip 130 acts as a wedge or camming surface and causes a partial expansion of the opening 124. As shown in FIG. 3B, this dimensional arrangement causes the lamina 120 to move posteriorly away from the vertebral body 122 as the implantable device 100 is inserted, hinging about the blind recess 118. Although in the illustrated embodiment the dimension Y of the shaft 104 is greater than the width of the opening 124, this need not always be the case. Rather, the dimension Y can be less than or substantially the same as the width of the opening 124, allowing the implantable device 100 to be inserted in a clearance fit.

Figure 3C:
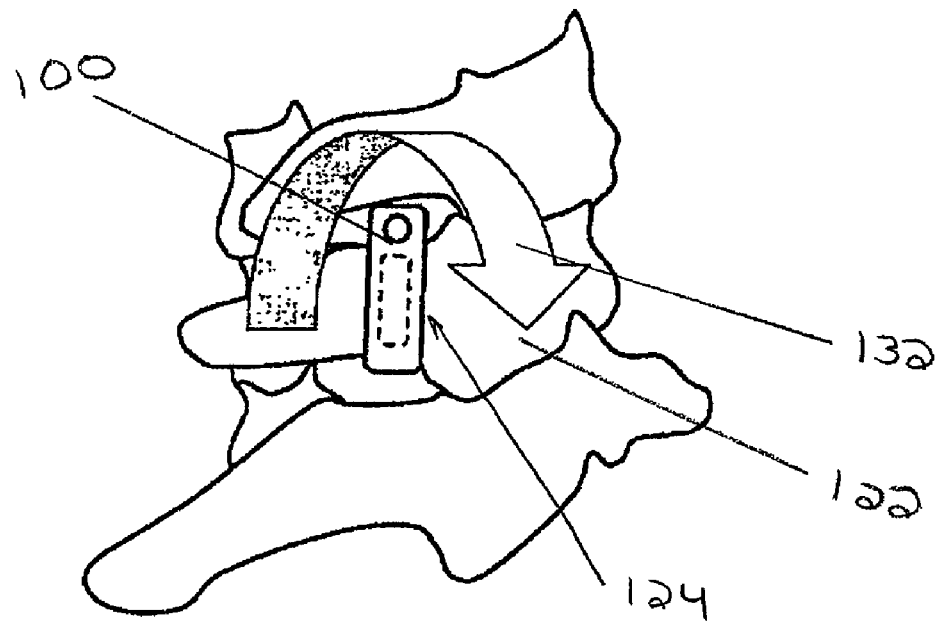
FIG. 3C is an elevation view of the vertebral body of FIG. 3A with the implantable device positioned in a first orientation within the opening in the lamina.
Figure 3D:
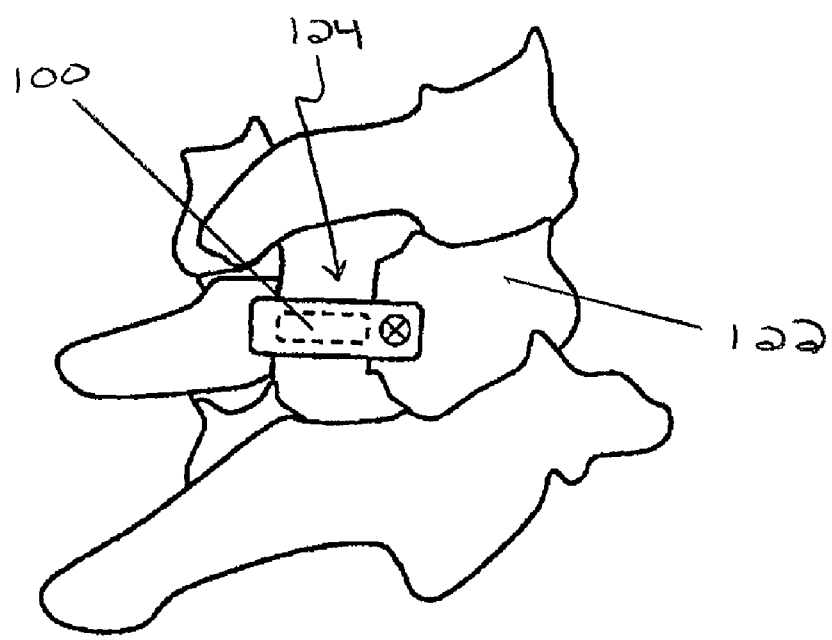
FIG. 3D is an elevation view of the vertebral body of FIG. 3A with the implantable device rotated 90 degrees clockwise to a second orientation within the opening in the lamina.
Figure 3E:
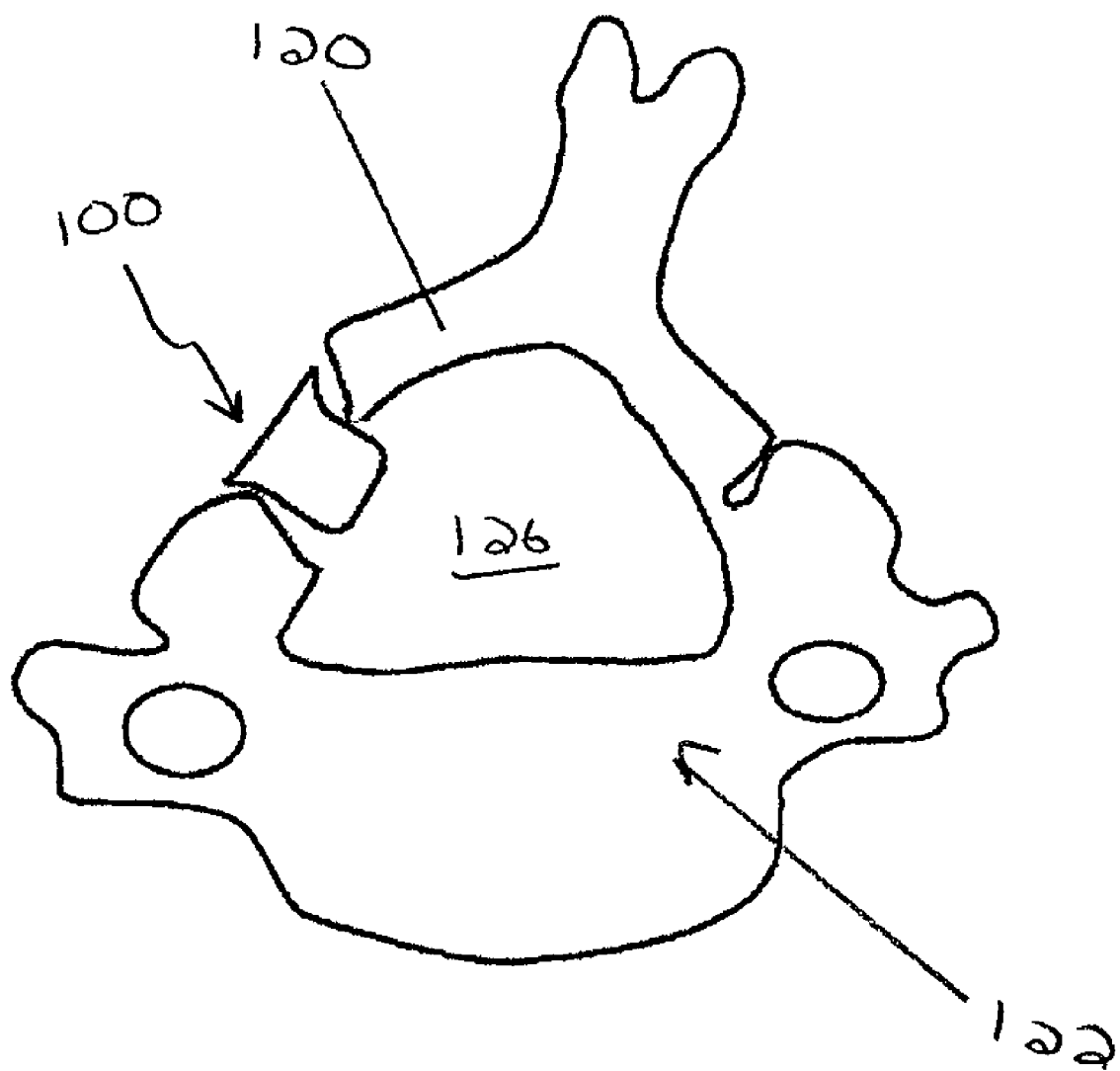
FIG. 3E is a plan view of the vertebral body of FIG. 3A after the implantable device has been rotated 90 degrees clockwise within the opening in the lamina.

With the implantable device 100 inserted into the opening 124, it can then be rotated in the direction of arrow 132, as shown in FIGS. 3B-3E. The implantable device 100 is shown in FIG. 3C inserted into the opening 124 in a first orientation. In FIG. 3D, the implantable device 100 is shown after having been rotated ninety degrees. As shown, because the shaft 104 of the implantable device 100 has a cross-section with a first dimension distinct from a second dimension, rotation of the device 100 within the opening 124 causes the width of the opening to expand. As shown in FIG. 3E, the lamina 120 is pushed further away from the vertebral body 122 by rotation of the implantable device 100, resulting in an increase in the cross-sectional size of the spinal canal 126.

Figure 4A:
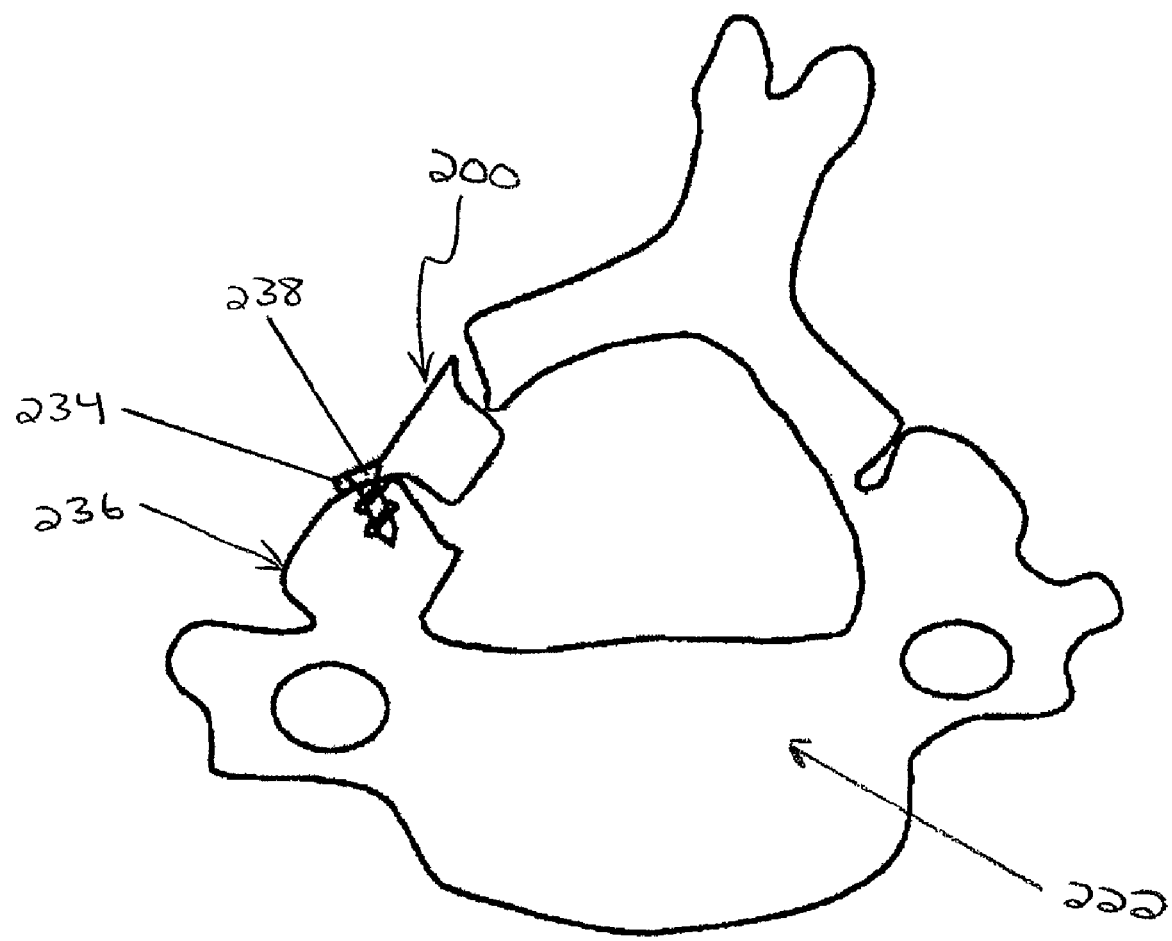
FIG. 4A is a plan view of a vertebral body and one embodiment of an implantable device having a lateral extension.
Figure 4B:
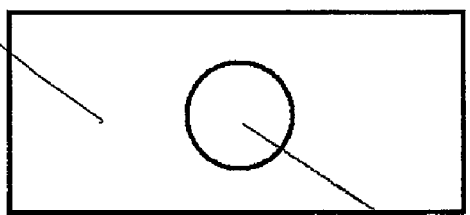
FIG. 4B is a plan view of one embodiment of the lateral extension of FIG. 4A.
Figure 4C:
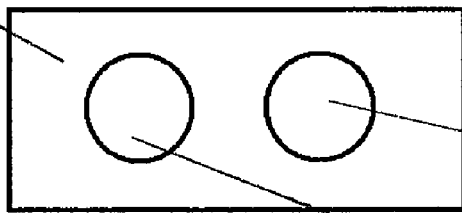
FIG. 4C is a plan view of another embodiment of the lateral extension of FIG. 4A.
Figure 4D:
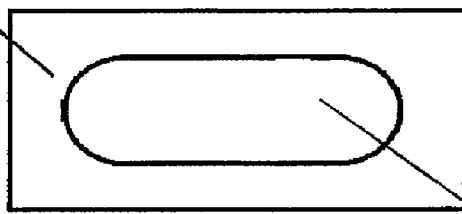
FIG. 4D is a plan view of another embodiment of the lateral extension of FIG. 4A.
Figure 4E:
FIG. 4E is a partial cross-sectional view of another embodiment of the lateral extension of FIG. 4A having a polyaxial fastener inserted therethrough.

In one exemplary embodiment, either the shaft or the head of the implantable device can include at least one lateral extension extending from a proximal end thereof to facilitate securing the implantable device to bone. In FIG. 4A, an implantable device 200 is shown having a lateral extension 234. The lateral extension 234 extends from a proximal end of the implantable device 200 over an outer bone surface 236 of the vertebral body 222. The lateral extension 234 can include at least one opening formed therein for receiving at least one fastening element 238. In the illustrated embodiment, the fastening element 238 is a threaded bone screw. A person skilled in the art will recognize however that virtually any type of fastening element known in the art can be employed to secure the implantable device 200 to the vertebral body 222. For example, the fastening element 238 can be a nail, hook, rivet, staple, etc. In another embodiment, the lateral extension 234 can be configured to receive more than one fastening element, or the implantable device 200 can have more than one lateral extension. As shown in FIGS. 4B-4E, the at least one opening in the lateral extension can have a variety of forms. In FIG. 4B, one embodiment of a lateral extension 234 is shown that has a single opening 240 formed therein. The opening 240 is a round bore hole that can conform to the diameter of the fastening element to be used. In FIG. 4C, another embodiment of a lateral extension 234' is shown that has multiple openings 240' therein. FIG. 4D shows yet another embodiment of a lateral extension 234" wherein the opening 240" is in the form of an elongate slot. Such embodiments provide for increased flexibility in the placement of the fastening element, since the fastening element can be placed anywhere along the length of the elongate slot. In FIG. 4E, another embodiment of a lateral extension 234''' is illustrated that has an opening 240''' configured to allow polyaxial fastening of the implantable device to bone. As shown in FIG. 4E, the proximal surface of the lateral extension 234''' has a spherical recess 242 formed therein for receiving the head of a polyaxial fastener 243. In addition, the distal surface of the lateral extension 234''' has a corresponding frusto-conical recess 244 configured to further increase the range of angles at which a polyaxial fastener 243 can be inserted through the lateral extension 234'''. Embodiments of the lateral extension can also include any combination of the various opening types described herein.

Figure 5A:
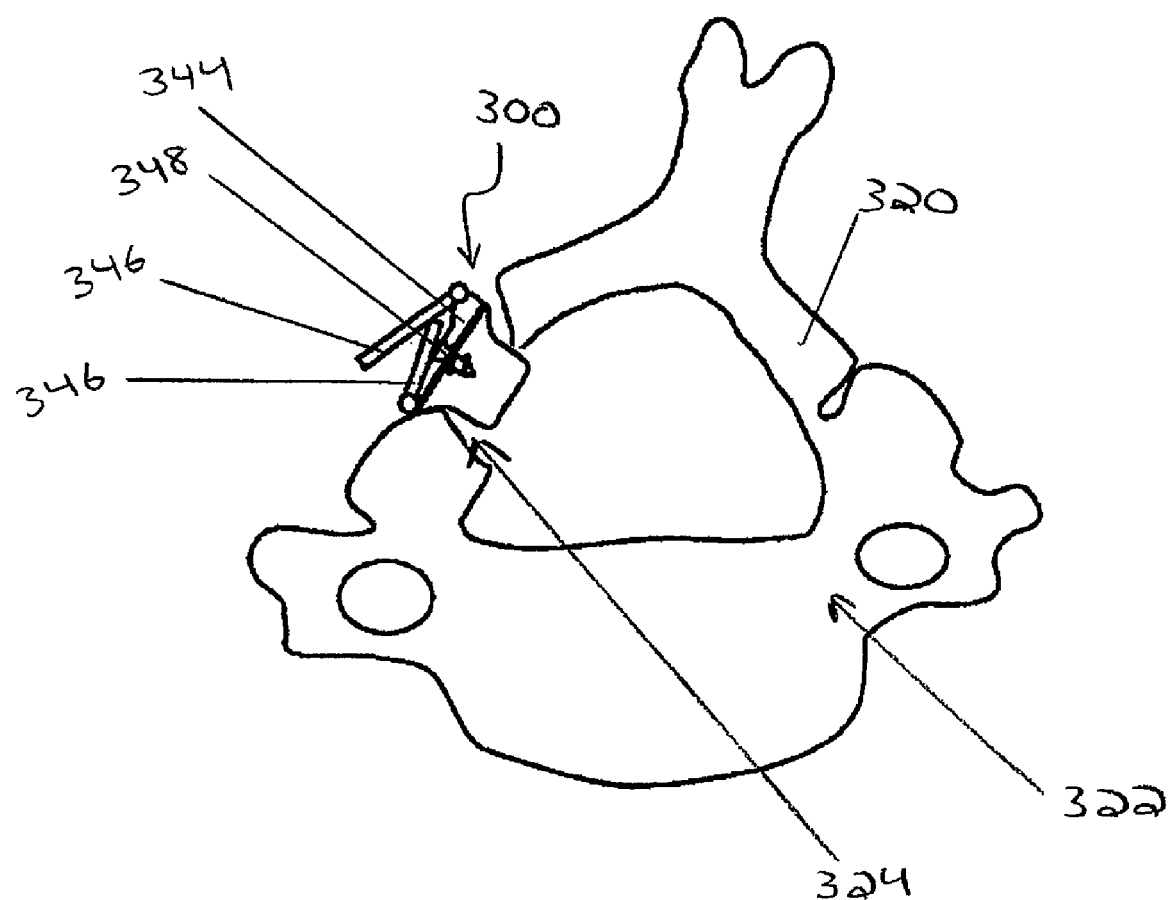
FIG. 5A is a plan view of a vertebral body and one embodiment of an implantable device having hinged lateral extensions.
Figure 5B:
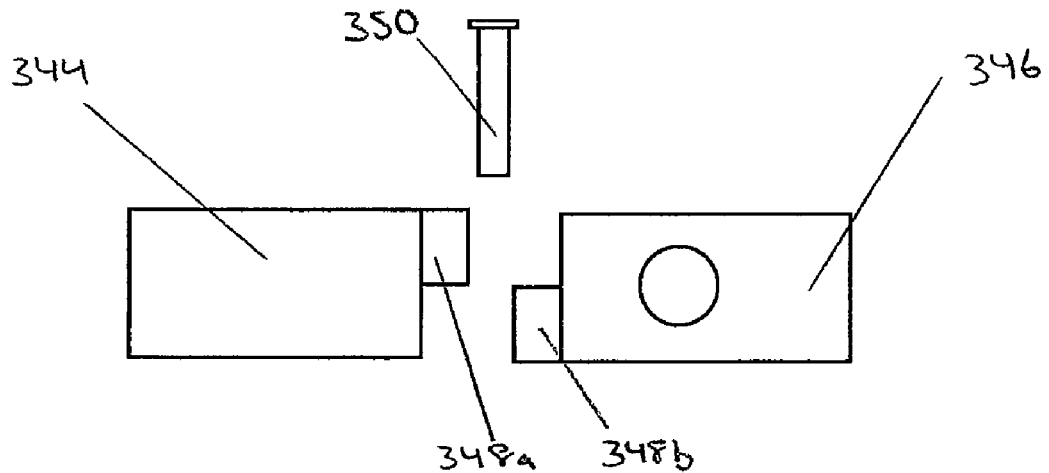
FIG. 5B is an exploded plan view of one embodiment of a hinge.
Figure 5C:
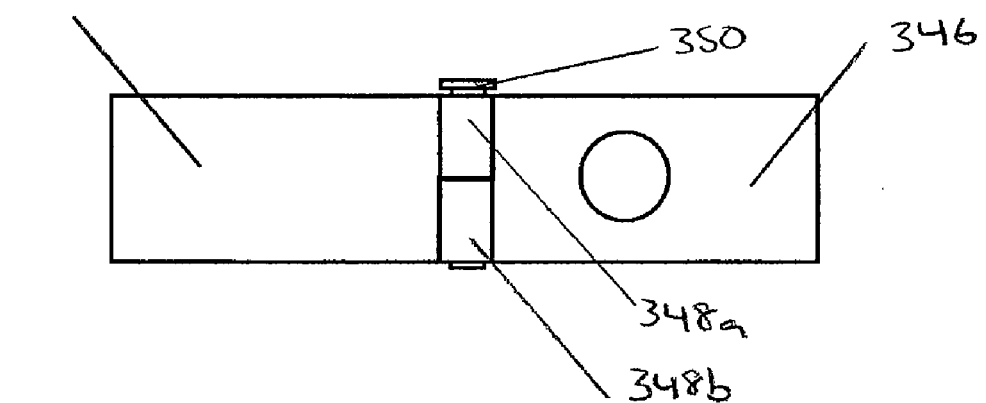
FIG. 5C is an assembled plan view of the hinge of FIG. 5B.
Figure 5D:
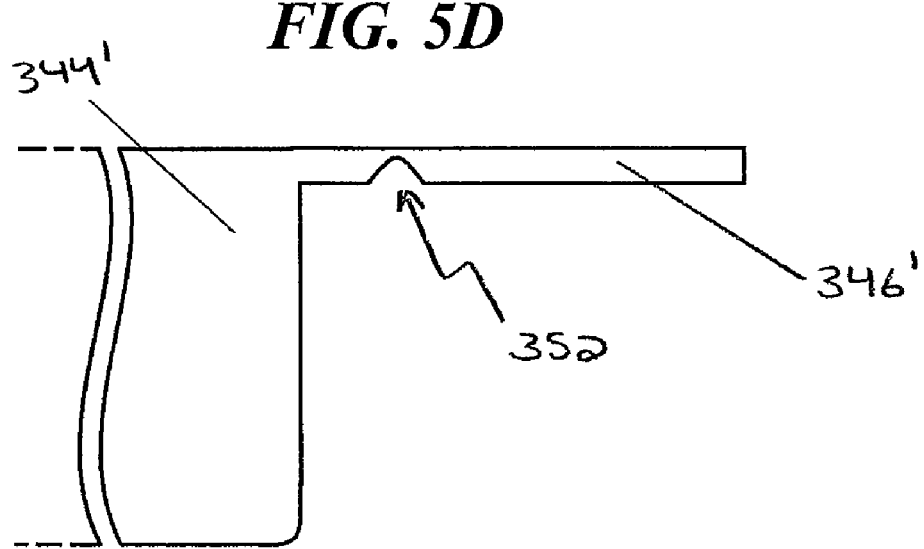
FIG. 5D is a plan view of another embodiment of a hinge.

In yet another embodiment, the implantable device can include lateral extensions that are attached thereto with a hinge. An implantable device 300 is shown in FIG. 5A inserted into an opening 324 in a lamina 320. As shown, the implantable device 300 can include a hinge body 344 attached to a proximal end of its head 302. The hinge body 344 can have one or more hinged plates 346 attached thereto. The hinge body 344 can be integral with the implantable device 300, can be permanently attached thereto, or can be selectively attached thereto. In the illustrated embodiment, the hinge body 344 is selectively attached to the implantable device 300 using a fastening element 348. Other means of attachment include riveting, stapling, gluing, welding, sonic welding, or any other attachment means known in the art. In addition, the hinge plates 346 can be attached to the hinge body 344 using a variety of hinge types. In one embodiment, as shown in FIGS. 5B and 5C, the hinge body 344 and the hinge plate 346 can each include one or more corresponding tubular protrusions 348a, 348b through which a hinge pin 350 can be inserted to form a hinge between the hinge body 344 and the hinge plate 346. In another embodiment, as shown in FIG. 5D, the hinge body 344' and the hinge plate 346' can be formed integrally and can have an area of decreased thickness 352 along which the two may hinge.

Figure 5E:
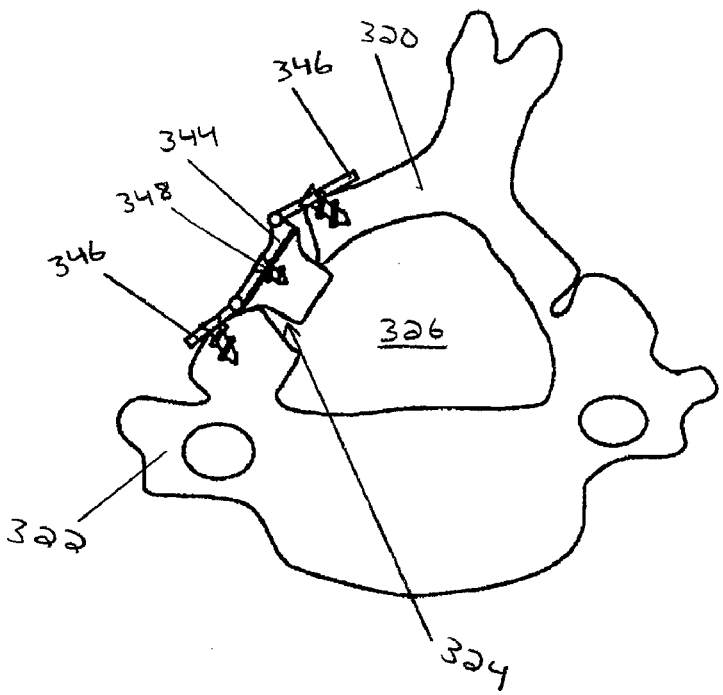
FIG. 5E is a plan view of the vertebral body and implantable device of FIG. 5A with the hinged lateral extensions unfolded.

The hinge plates 346 are shown in FIG. 5A in a first, folded position and again in FIG. 5E in a second, unfolded position. As shown, when the hinge plates 346 are unfolded, they can be fastened to a portion of the lamina 320 and/or the vertebral body 322 adjacent to the opening 324 using any of a variety of known fasteners, such as bone screws, rivets, staples, etc. The hinge plates 346 can have openings formed therein as described above with respect to the lateral extensions 234 shown in FIGS. 4A-4E.

Figure 5F:
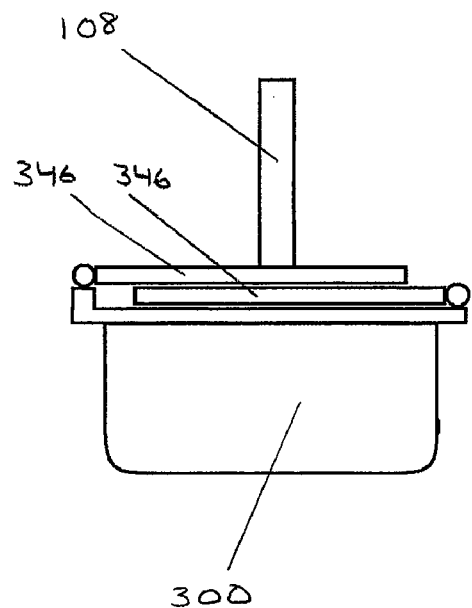
FIG. 5F is an elevation view of the implantable device of FIG. 5A with one embodiment of an insertion apparatus selectively coupled thereto.
Figure 5G:
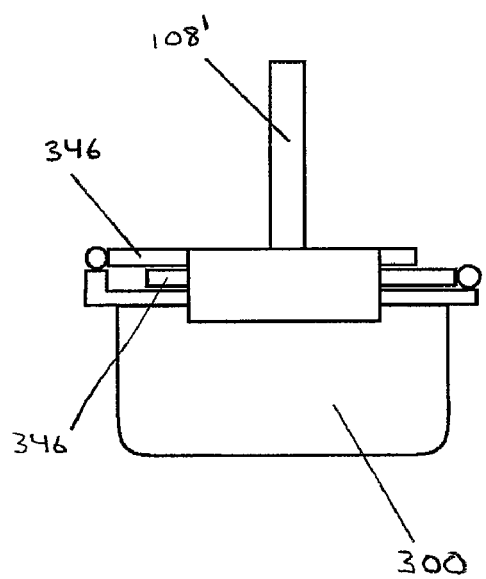
FIG. 5G is an elevation view of the implantable device of FIG. 5A with another embodiment of an insertion apparatus selectively coupled thereto.

In use, the implantable device can be inserted into the opening 324 and rotated to push the lamina 320 away from the vertebral body 322, thereby expanding the cross-sectional size of the spinal canal 326. The hinge body 344 and hinge plate 346 assembly can then be positioned adjacent to the implantable device 300 and affixed thereto using a fastener 348. The hinge plate(s) 346 can then be unfolded and fastened to the vertebral body 322 and/or the lamina 320. In embodiments where the hinge body 344 is formed integrally with the implantable device 300, the openings in the hinge plate(s) 346 can be sized to permit an insertion apparatus 108 to be passed through the folded hinge plate(s) 346 and to selectively couple to the implantable device 300, as shown in FIG. 5F. Alternatively, when an insertion apparatus 108' is used, the hinge plate(s) 346 can be sized such that the opposed claws of the insertion apparatus 108' can be selectively coupled to the implantable device 300, around the hinge plate(s) 346 when they are in a folded position, as shown in FIG. 5G. One advantage to the hinge plate embodiments is that the implantable device and/or hinge body and hinge plate assembly can be inserted through the narrow confines of a working channel of a minimally invasive access device, such as a cannula or tubular port.

Figure 6A:
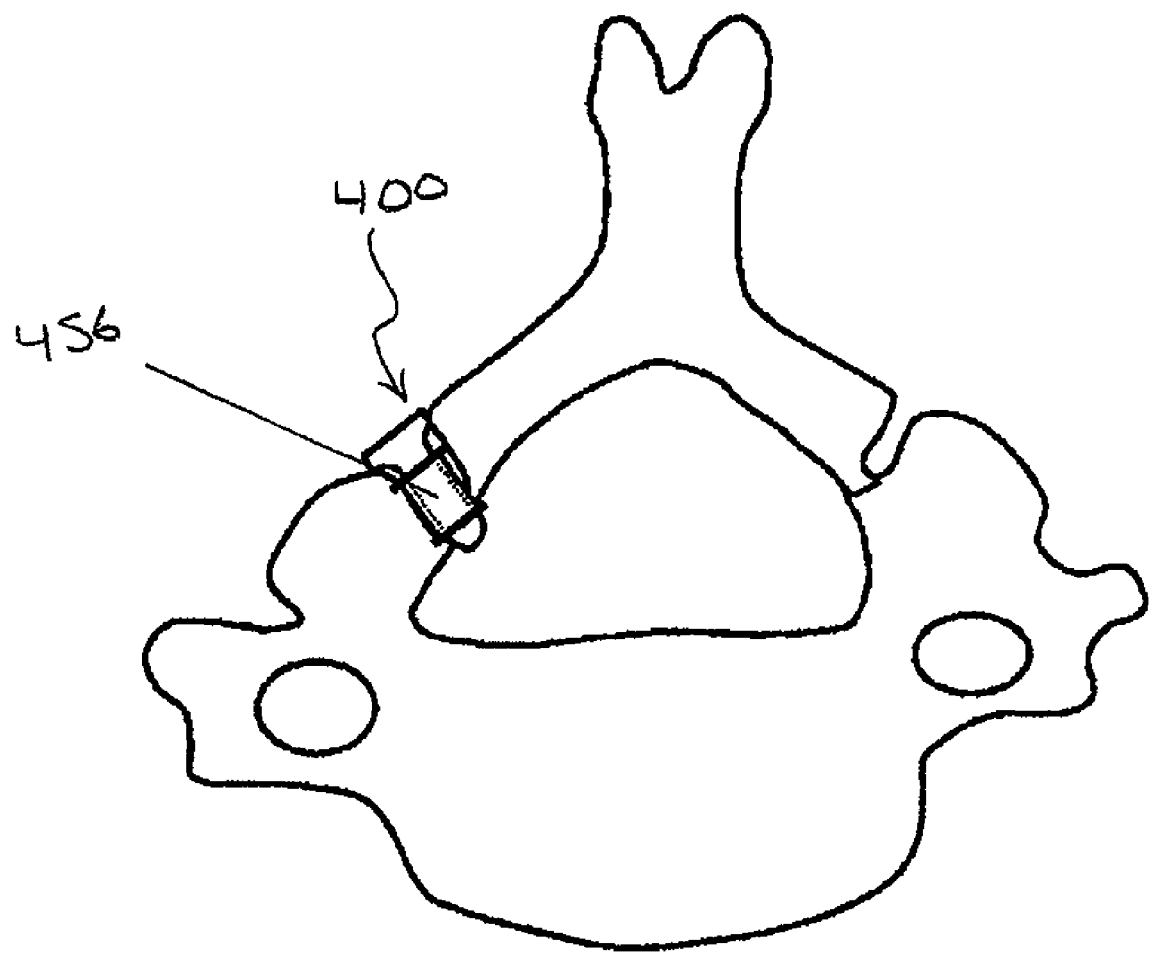
FIG. 6A is a plan view of a vertebral body and one embodiment of an implantable device having a sleeve disposed therearound.
Figure 6B:
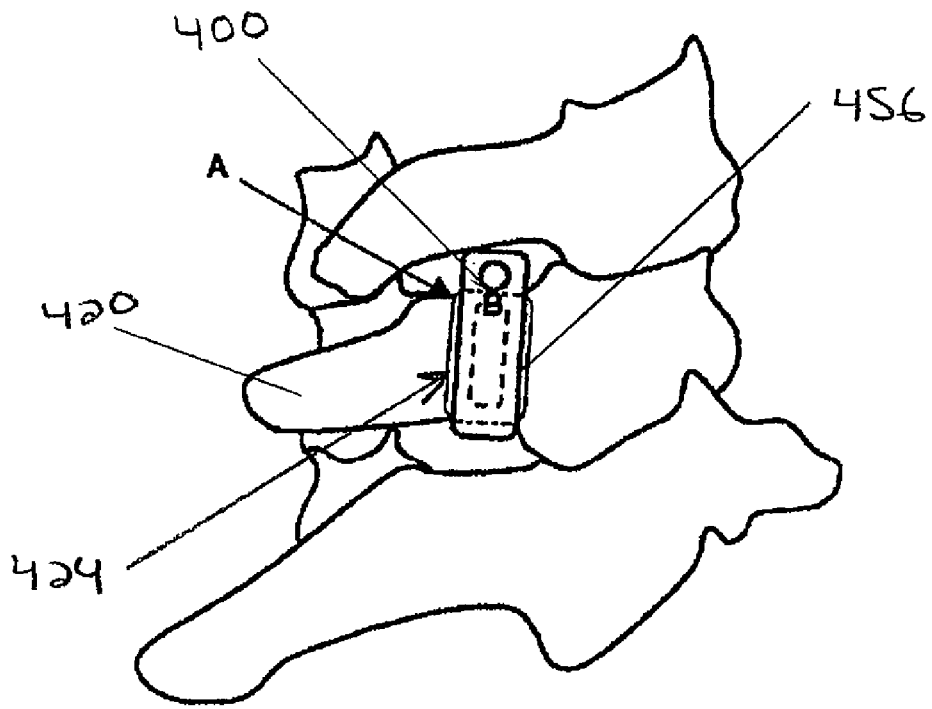
FIG. 6B is an elevation view of the vertebral body and implantable device of FIG. 6A.
Figure 6C:
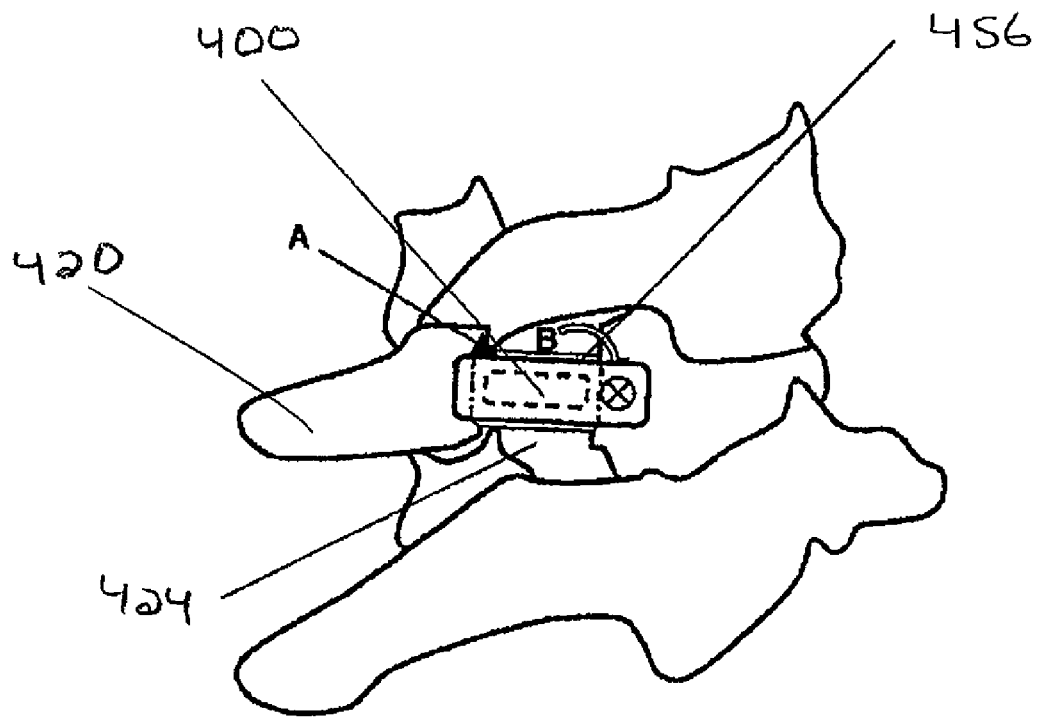
FIG. 6C is an elevation view of the vertebral body and implantable device of FIG. 6A, after the implantable device is rotated 90 degrees clockwise.
Figure 6D:
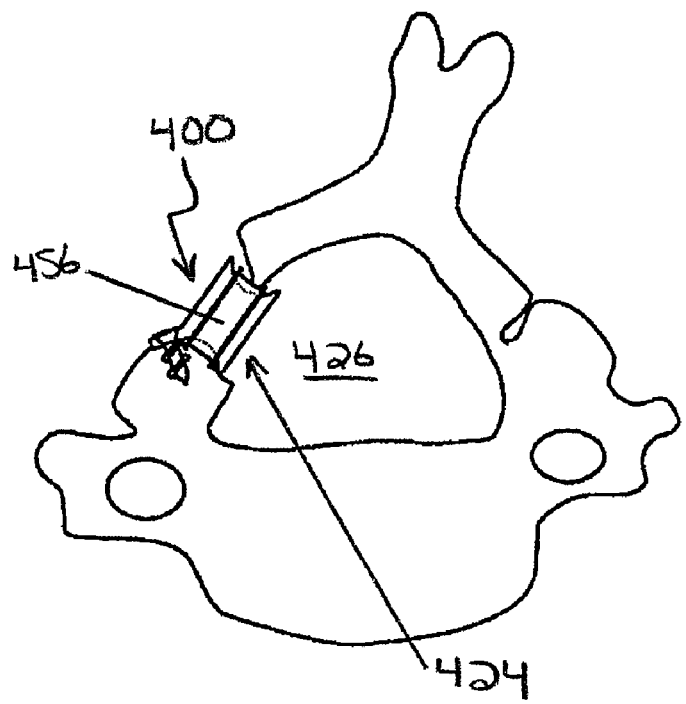
FIG. 6D is a plan view of the vertebral body and implantable device of FIG. 6A after the implantable device is rotated 90 degrees clockwise.

In another embodiment, as shown in FIG. 6A, the implantable device 400 can include a sleeve 456 disposed therearound. As shown in FIGS. 6B-6C, the sleeve 456 can be configured to remain in a fixed position within the opening 424 in the lamina 420 while the implantable device 400 is free to rotate. In the illustrated embodiment, a point A on the sleeve 456 is shown to remain in the same position, despite the implantable device 400 having been rotated 90 degrees in the clockwise direction. In such embodiments, the implantable device frictionally slides along an interior surface of the sleeve 456, rather than along an interior surface of the bone opening 424. The sleeve 456 can be formed of a low-friction material or can include a low-friction coating applied thereto, thereby reducing the rotational force required to manipulate the implantable device 400. Alternatively, or in addition, part or all of the surface of the sleeve 456 can be coated or formed from an osteointegration promoting material such as HEALOS. One skilled in the art will appreciate that a variety of biocompatible materials can be used to form the sleeve, including metals, metal alloys, polymers, and ceramics. As shown in FIGS. 6B-6D, the sleeve 456 can be expandable and/or flexible so that when the implantable device 400 is rotated to expand the spinal canal 426, the sleeve 456 likewise expands and otherwise remains in position within the opening 424.

In use, the sleeve 456 can be positioned around and/or pre-attached to the implantable device 400 first, and the two can then be inserted as a pair into the opening 424. Alternatively, the sleeve 456 can be first inserted by itself in the opening 424 and then the implantable device 400 can be inserted within the sleeve 456 thereafter. In the latter embodiment, the sleeve 456 can have a flanged portion at its proximal end (not shown) sized larger than the width of the opening 424 to prevent over-insertion of the sleeve 456 into the spinal canal 426, similar to the proximal head of the implantable device discussed above.

Various methods for expanding a spinal canal are also provided. In one embodiment, a patient's spine is accessed using one or more minimally-invasive techniques known in the art. For example, a small incision can be made in a patient's neck or back and a trocar or cannula can be inserted therethrough to provide a working channel through which a surgeon can access the patient's spine. The surgeon can then pass one or more suitable instruments through the working channel to form an osteotomy or opening in one side of a lamina of one of the patient's vertebrae. The osteotomy can be in the form of an opening formed all the way through the lamina to the dura of the spinal canal. Using the same or a second access portal, the surgeon can also form a blind bore or "green stick" in a second side of the lamina to act as a hinge.

With the patient's vertebra prepared as described, the surgeon can insert an implantable device (e.g., using the same cannula used to access the surgical site and form the osteotomy) described herein into the osteotomy. The surgeon can first selectively couple the implantable device to an insertion apparatus as described above and then pass the elongate body of the insertion apparatus and the implantable device through the working channel, keeping the handle and trigger of the insertion apparatus outside of the patient. Using an imaging technique such as fluoroscopy and/or mechanical feedback, the surgeon can advance the distal bulleted tip of the implantable device into the osteotomy. In one embodiment, the implantable device and osteotomy can be sized such that merely inserting the implantable device, without rotating it, is effective to partially expand the osteotomy and the spinal canal. Alternatively, the implantable device can be sized to fit within the osteotomy in a clearance fit. The implantable device can be advanced distally into the osteotomy until the head of the device contacts an outer surface of the vertebra, preventing further distal advancement of the implantable device. The surgeon can then rotate the handle of the insertion apparatus 90 degrees, effecting a similar 90 degree rotation of the implantable device within the osteotomy. Since the shaft of the implantable device has a first dimension distinct from a second dimension, rotation thereof within the osteotomy can cause the osteotomy and therefore the spinal canal to expand in size.

In some embodiments, rotating the implantable device within the osteotomy can cause one or more arcuate protrusions formed on the implantable device to bite into the surrounding bone, thereby minimizing the risk of undesirable post-operative movement of the device. Rotating the implant can also cause the cut ends of the lamina on either side of the osteotomy to cam over one or more radiused edges of the implantable device.

Having rotated the implantable device 90 degrees, the surgeon can actuate a component (e.g., a trigger) of the insertion apparatus to detach it from the implant. The insertion apparatus can then be withdrawn from the working channel, leaving the implantable device in the patient's spine. The surgeon can then remove any other tools or devices used in the procedure and close the incision(s).

In some embodiments, methods for expanding the spinal canal can include securing the implant to bone to prevent post-operative movement of the implantable device. In such embodiments, the surgeon can pass a fastener through the working channel and can fasten a lateral extension of the implantable device to a bone surface adjacent to the osteotomy. In another embodiment, securing the implant to bone can include unfolding one or more hinged lateral extensions and then fastening them to adjacent bone as described herein. The hinged lateral extensions can be formed integrally with the implantable device, in which case the device can be initially passed through the working channel with the hinged extensions in a folded position using an insertion apparatus similar to that described above in FIGS. 5F and 5G. In embodiments where the hinged lateral extensions are not formed integrally with the implantable device, the device can optionally be implanted first by itself. The surgeon can then pass the hinged lateral extensions and/or the hinge body through the working channel and attach them to the implantable device already inserted into the patient's spine.

Methods for expanding the spinal canal can also include the use of a sleeve disposed around the implantable device to allow the implant to rotate within the sleeve rather than within the opening in the lamina. In one embodiment, the sleeve can be positioned around the implantable device prior to inserting it into the opening in the lamina. Once the sleeve and the implantable device are simultaneously inserted, the sleeve can stay in position while the implantable device is rotated therein. In another embodiment, the sleeve can be inserted into the osteotomy first, prior to inserting the implantable device. In such embodiments, the surgeon can advance the sleeve distally into the osteotomy until a flanged portion at the proximal end of the sleeve contacts the outer surface of the lamina, preventing further distal advancement. The implantable device can then be advanced into the sleeve and rotated as described above.

Figure 7:
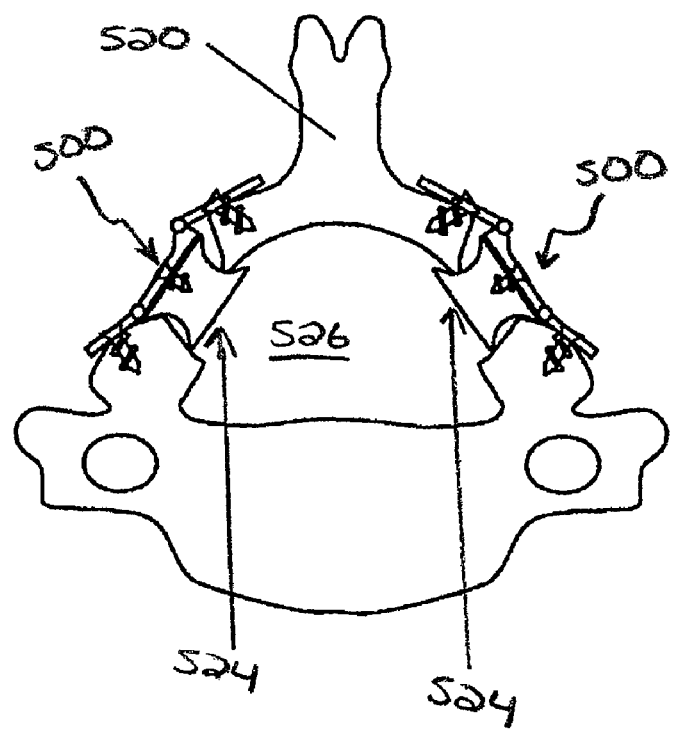
FIG. 7 is a plan view of a spinal canal having been expanded using two of the implantable devices of FIG. 5A.

In some embodiments, methods for expanding the spinal canal can include bilaterally expanding the spinal canal by distracting the lamina from both sides. As shown for example in FIG. 7, two osteotomies 524 can be formed, one on each side of the lamina 520. Two implantable devices 500 can then be used to bilaterally expand the spinal canal 526, substantially as described above with respect to single-implant embodiments. Although an implantable device having hinged lateral protrusions is illustrated, any embodiment of the implantable device can be used for bilaterally expanding the spinal canal. In addition, the bilateral expansion need not always be symmetrical as shown. Rather, implantable devices of differing sizes may be used on either side of the vertebra to achieve an asymmetrical distraction of the lamina.

While use of the implantable device in the spine is discussed at length herein, the device can be used in almost any portion of a patient, and its use is not by any means limited to within the spine. Additionally, a person skilled in the art will appreciate that, while the methods and devices are described in connection with minimally invasive procedures, the methods and devices disclosed herein can be used in any kind of surgical procedure, including open surgery.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An implantable device for expanding a spinal canal, comprising:
   an elongate body having a head and a shaft and a longitudinal axis;
   the shaft having a cross-section taken perpendicular to the longitudinal axis such that the longitudinal axis is normal to a plane in which the cross-section lies, the cross-section having a length that is distinct from a width and having two diagonally-opposite radiused corners and two diagonally-opposite non-radiused corners, and the head having at a proximal end thereof a driver interface with a torque receiving surface;

wherein the head is formed at a proximal end of the elongate body and a distal end of the elongate body is bulleted.

2. The device of claim 1, wherein the cross-section of the shaft is substantially rectangular.

3. The device of claim 1, wherein the body includes an osteointegration-promoting coating.

4. The device of claim 1, wherein the head has a dimension larger than the shaft such that it is configured to prevent over-insertion of the body into an opening.

5. The device of claim 1, wherein the elongate body has at least one arcuate protrusion formed thereon configured to engage bone as the body is rotated within an opening.

6. The device of claim 1, further comprising a sleeve disposed around the body such that the body is rotatable within the sleeve.

7. The device of claim 1, wherein the body is formed of a resorbable material.

8. The device of claim 1, wherein the body includes at least one lateral extension at its proximal end, the lateral extension having at least one opening formed therein for receiving at least one fastening element.

9. The device of claim 8, wherein the opening in the at least one lateral extension comprises an elongate slot.

10. The device of claim 8, wherein the opening in the at least one lateral extension comprises a polyaxial seat.

11. The device of claim 8, wherein the at least one lateral extension is attached to the proximal end of the body with a hinge such that the extension is rotatable about the hinge.

* * * * *